US007041064B2

(12) United States Patent
Vayer

(10) Patent No.: US 7,041,064 B2
(45) Date of Patent: May 9, 2006

(54) ANIMAL DEVICE FOR COLLECTING AN ANIMAL'S SEMINAL FLUID

(75) Inventor: Gérard Vayer, Douai (FR)

(73) Assignee: Genes Diffusion, Douai (FR)

( * ) Notice: Subject to any disclaimer, the term of this patent is extended or adjusted under 35 U.S.C. 154(b) by 328 days.

(21) Appl. No.: 10/332,779

(22) PCT Filed: Aug. 10, 2001

(86) PCT No.: PCT/FR01/02601

§ 371 (c)(1),
(2), (4) Date: Jan. 10, 2003

(87) PCT Pub. No.: WO02/13723

PCT Pub. Date: Feb. 21, 2002

(65) Prior Publication Data

US 2004/0039248 A1 Feb. 26, 2004

(30) Foreign Application Priority Data

Aug. 11, 2000 (FR) .................................. 00 10604

(51) Int. Cl.
*A61B 10/00* (2006.01)

(52) U.S. Cl. ...................................................... 600/562

(58) Field of Classification Search ................ 600/562, 600/35, 33, 38, 573, 576, 578; 604/349, 604/347

See application file for complete search history.

(56) References Cited

U.S. PATENT DOCUMENTS

| | | | | |
|---|---|---|---|---|
| 2,686,519 | A | 8/1954 | Westerman | |
| 4,620,531 | A | 11/1986 | Dyer | |
| 5,437,652 | A | 8/1995 | Anatolievich | |
| 5,695,446 | A | 12/1997 | Lindholm-Ventola | |
| 5,961,503 | A * | 10/1999 | Simmet et al. | 604/349 |
| 2002/0133090 | A1 * | 9/2002 | Michelle | 600/562 |

FOREIGN PATENT DOCUMENTS

| | | | |
|---|---|---|---|
| EP | 0 699 422 | A | 3/1996 |
| FR | 946 822 | A | 6/1949 |
| WO | WO 92 19179 | A | 11/1992 |

* cited by examiner

*Primary Examiner*—Max F. Hindenburg
*Assistant Examiner*—Brian Szmal
(74) *Attorney, Agent, or Firm*—Egbert Law Offices

(57) ABSTRACT

The invention concerns a device for sampling animal seminal liquid, notably boar seminal liquid, exhibiting at least one housing capable of accommodating a penis and a trigger for ejaculation. According to the invention, the ejaculation trigger includes a mechanism to subject the walls of the housing to pulses intended for stimulating the penis. The invention also concerns a facility for collecting an animal seminal liquid including such a device and also a usage thereof or of said facility for collecting boar seminal liquid.

10 Claims, 3 Drawing Sheets

ANIMAL DEVICE FOR COLLECTING AN ANIMAL'S SEMINAL FLUID

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

The invention concerns a device for collecting animal seminal liquid, as well as a facility for collecting such a liquid, comprising such device and a usage of said device and/or said facility for collecting boar seminal liquid.

However, although more particularly suited for such applications, the invention could also be used for any other type of species, more particularly animal species.

BACKGROUND OF THE INVENTION

Currently, boar semen is collected manually. Such an operation is long and tedious, the more so with such specie because the process may take up to several minutes. Moreover, it raises hygiene problems.

For other species, mechanical devices have already been suggested for collecting seminal liquid. They remain nevertheless rudimentary since they generally address animals whereof the ejaculation time is very short, notably a few seconds, let alone a few fractions of a second as is the case for rabbits, horses or bulls.

The object of this invention is to offer a device for collecting animal seminal liquid, as well as a facility for collecting such a liquid, enabling to remedy the previous shortcomings and authorizing mechanized and automated intervention.

Another object of this invention is to offer a device for collecting animal seminal liquid, as well as a facility for collecting such a liquid which authorizes interventions with high hygienic level.

Another object of this invention is to offer a device for collecting animal seminal liquid, as well as a facility for collecting such a liquid, which enable to do away with the use of a heat-exchanging fluid heated to cause ejaculation, since heat is a spermicidal agent.

Another object of this invention is offer a device for collecting animal seminal liquid, as well as a facility for collecting such a liquid, which may operate reliably and reproducibly over an extended period of time.

Other objects and advantages of the invention will appear in the following description, given only for exemplification purposes and without being limited thereto.

BRIEF SUMMARY OF THE INVENTION

The invention relates first of all to a device for sampling animal seminal liquid, notably boar seminal liquid, exhibiting at least one housing capable of accommodating the penis and means to trigger the ejaculation, characterized in that said ejaculation-triggering means are composed of means to subject the walls of said housing to pulses intended for stimulating the penis.

The invention also concerns a facility for collecting an animal seminal liquid, notably boar seminal liquid, comprising such a device.

The invention also concerns a usage of the device and of the facility described above for collecting boar seminal liquid.

BRIEF DESCRIPTION OF THE SEVERAL VIEWS OF THE DRAWINGS

The invention will be understood better when reading the following description, accompanied by the appended drawings.

DETAILED DESCRIPTION OF THE INVENTION

The invention concerns first of all a device for collecting animal seminal liquid.

As illustrated on FIGS. 1 to 5, it comprises at least a housing 1, capable of accommodating the penis, and means to trigger the ejaculation.

According to the invention, said elements are composed of means 2 to subject the walls of said housing 1 to pulses intended for stimulating the penis.

They are for example pulses controlled manually or automatically according to a chosen cycle, notably intended for simulating the uterine contractions of the female.

One may choose, for exemplification purposes, to exert a first pressure for the mating of the penis in the housing, then a constant pressure during mating, and then several sporadic pressures during the collection to maintain the stimulation.

One obtains therefore a mechanized device, which may even be automated.

Said housing 1 extends, for instance, longitudinally between an introduction orifice 3 of the penis and an evacuation orifice 4 of the seminal liquid.

Said ejaculation-triggering means are then capable of causing a substantially radial deformation of the walls of said housing 1, over their whole length, notably in the manner of sporadic pressures.

Said housing 1 emulates, for example, the shape of the vagina of the female of the corresponding specie.

Figure 1:
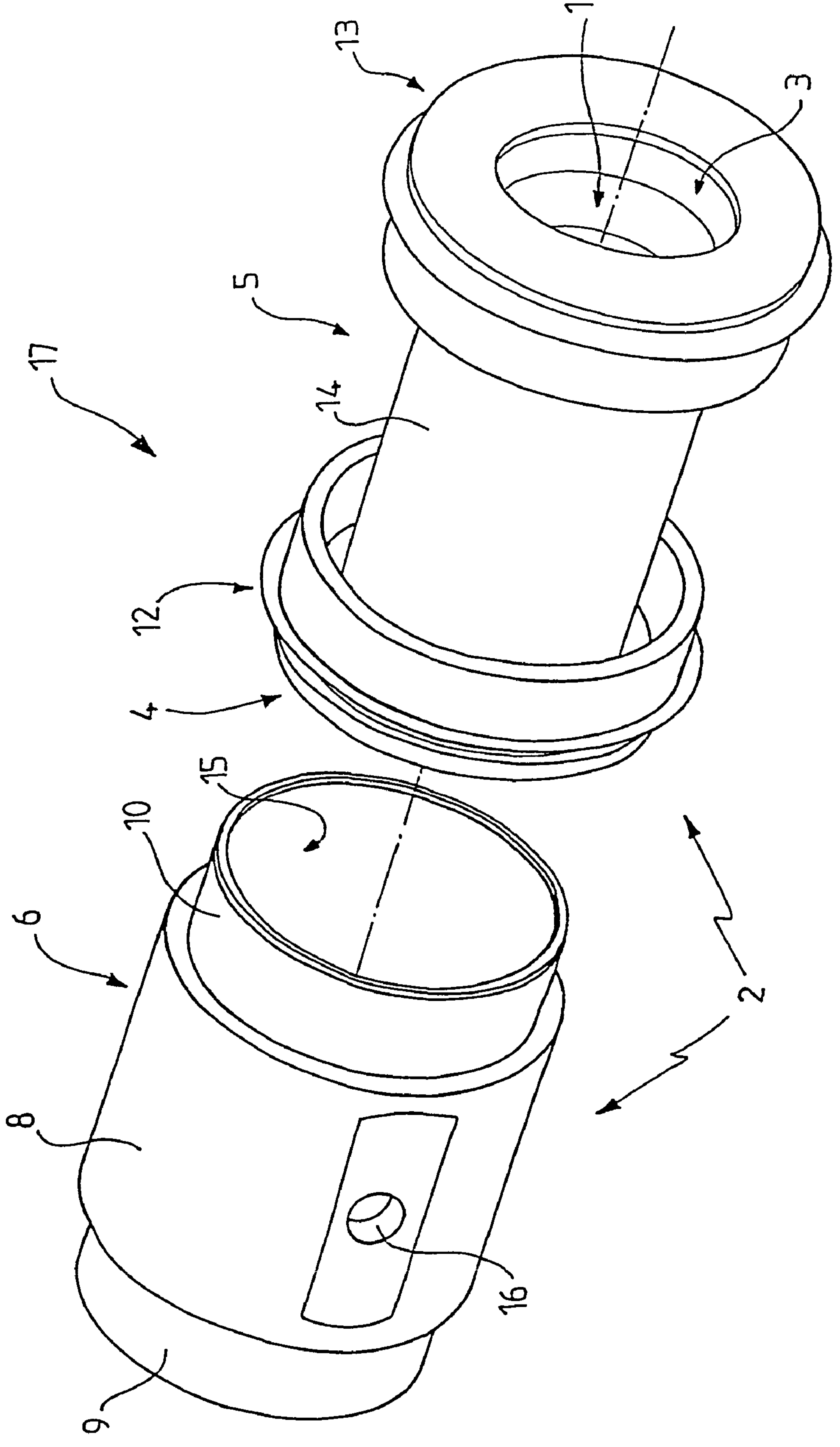
FIG. 1 is an exploded perspective view of an exemplary device for collecting seminal liquid according to the invention.
Figure 2:
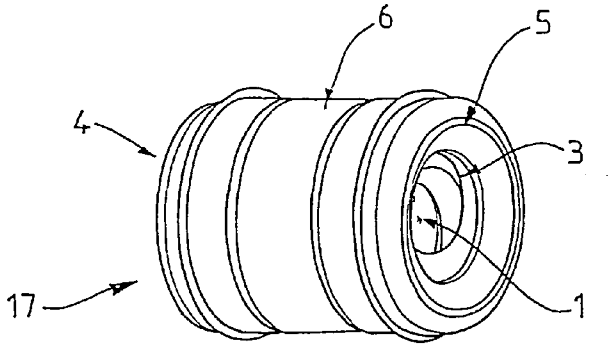
FIG. 2 is a side perspective view of such a device, once assembled.
Figure 3:
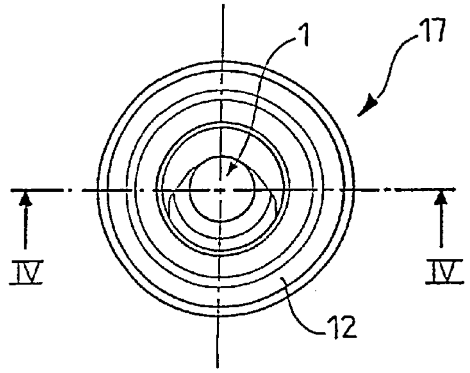
FIG. 3 is a front view according to FIG. 2.
Figure 4:
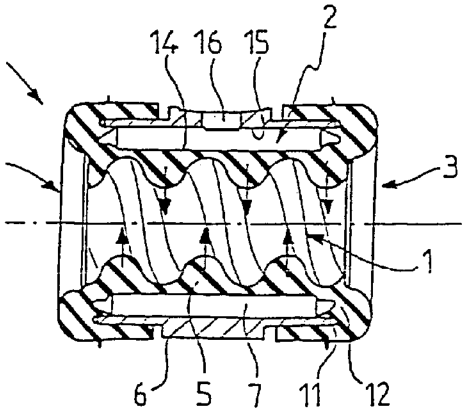
FIG. 4 is a sectional view along the line IV—IV represented on FIG. 3.
Figure 5:
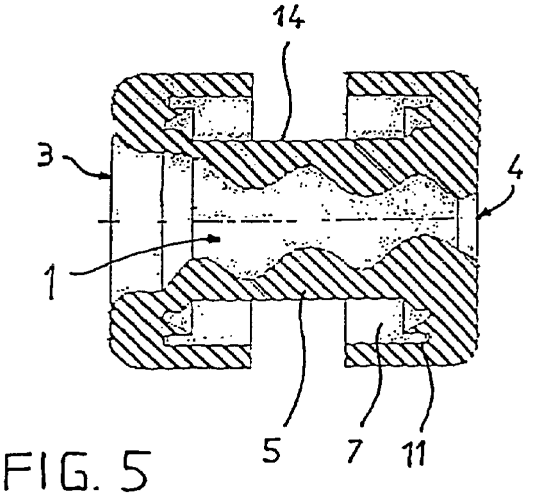
FIG. 5 is a sectional view of an embodiment variation of an element of FIG. 4.

As will appear more particularly on FIGS. 4 and 5, it may then be, notably substantially helicoidal in shape, suited to the penis of the boar.

In this sense, said housing is defined, for example, by a three step helix. It is notably 60 to 80 mm in length, for instance about 65 mm. Such a length enables the device to act upon the active portion of the penis of the boar, notably by letting its end protrude. It also enables to ensure good introduction of the penis and promotes the handability of the device.

Said device is composed, for example, of a tubular flexible membrane 5, delineating internally said housing 1, and a rigid sheath 6, also tubular and receiving internally said membrane 5. Said membrane 5 and said sheath 6 delineate together a sealed air chamber 7 and said device comprises moreover means, not represented, to vary the pressure of the air in said chamber. In a manner known to the man of the art, they may be any pressurized air supply means. The result is then a reliable and heavy-duty device.

The pressure applied in said chamber is, for example, homogeneous over its whole length.

So, advantageously, said means to subject the walls of said housing to pulses intended for stimulating the penis are provided, enabling localized stimulation thereof, notably close to its extremity.

Thus, the penis may be highly stimulated as of the applications of the first pressures and proper mating can be guaranteed.

As illustrated on FIG. 5, to enable such localized stimulation, said housing 1 exhibits locally a narrowed section, notably at the evacuation orifice 4 of the seminal liquid. Thus, although the pressure applied in the chamber 7 is homogeneous, a pressure gradient may be obtained at the penis.

More accurately, said housing 1 exhibits for example a decreasing section from said inlet orifice 3 to said evacuation orifice 4. Said housing is thus delineated notably by the volume described by a circle whereof the center follows a helicoidal path along the longitudinal axis of the membrane, whereas said circle remains orthogonal to said longitudinal axis. Said circle also exhibits a decreasing radius from said introduction orifice to said evacuation orifice. Said helicoidal path may exhibit a constant radius or a radius decreasing from said introduction orifice to said evacuation orifice.

Such a shape, which delineates a truncated aperture, facilitates the penetration of the penis. Consequently, the outlet orifice will remain sufficiently large in order to prevent the penis from being blocked.

Said housing may also be extended axially by a cylindrical portion delineated by an annular axial extension of the membrane 5, not represented, at either of its ends. Said device may also comprise means for pinching said extensions, intended for increased stimulation of the penis.

Said membrane is composed, for instance, of a mixture of silicon and oil.

The flexibility of said membrane 5 enables to provide the requested deformations under the effect of the air injected into said chamber 7.

Said sheath 6 is, for example, cylindrical. It is composed notably of a body 8 and of longitudinal ends 9, 10 of smaller thicknesses.

Said membrane 5 nests onto said sheath 6 at its longitudinal ends 9, 10. To this end, it is fitted with an annular groove 11 situated at the extreme poles 12, 13. The latter may cover said longitudinal ends 9, 10 of the sheath, in order to confer homogeneous external aspect to the device.

Said membrane may be attached to the body using two flexible clamps ensuring, with two coaxial lips provided on said membrane, at each longitudinal end of said chamber, good tightness of said chamber.

Said membrane 5 exhibits, notably, a cylindrical external face 14 delineating with the internal face 15 of the body of the sheath, said chamber 7. Said membrane 5 and said sheath 6 may be coaxial.

As already evoked, the internal face of said membrane can be adapted according to the specie in question. As regards the external face of the sheath, it can be fitted, at the body 8, with an air introduction orifice 16 between said chamber 7.

Said flexible membrane 7 may be capable of being coated with a protection film, more commonly called a single use condom. Thus, the interventions will be more hygienic. Said condom is open at both its longitudinal ends, whereas said ends can be folded up at the longitudinal ends of the body 8 to attach said condom.

Said device can be fitted with a handling grip, for example attached to said body. Said grip will make the handling easier when inserting the penis into the device. Said grip may integrate control means to vary the pressure in the chamber 7, for example using two knobs to adapt the pressure cycle.

Figure 6:
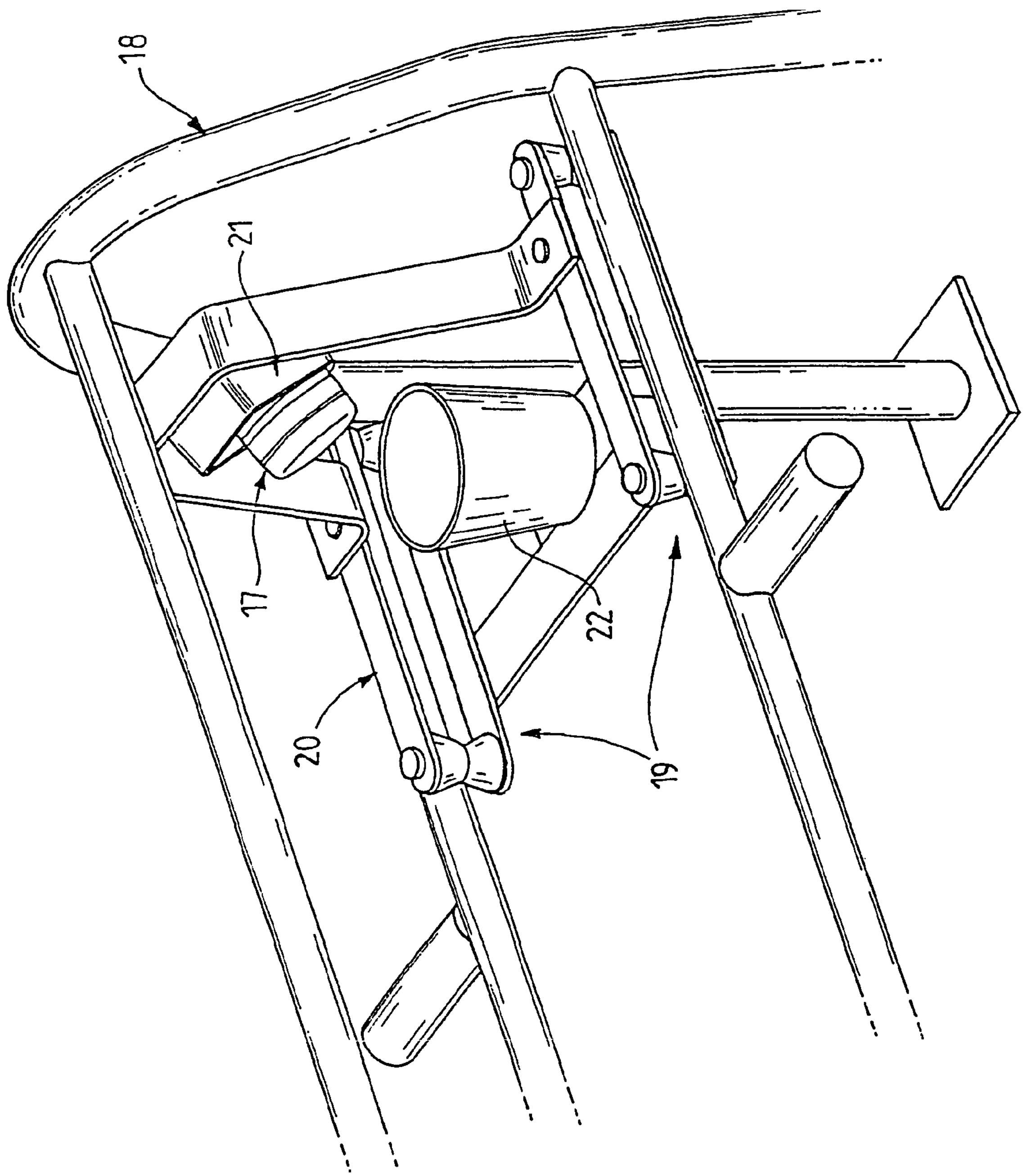
FIG. 6 is an upper perspective view of an embodiment example of the seminal liquid collection facility according to the invention.

As illustrated on FIG. 6, the invention also concerns a facility for collecting animal seminal liquid comprising a device 17 for sampling such a liquid, as described above. With such a facility, the operator need not hold said device 17 any longer.

Said facility comprises, for instance, a reinforcement 18, notably tubular, intended for simulating the presence of the female, whereby the operator's interventions are then reduced to a minimum.

Said device 17 can be mounted mobile with respect to said reinforcement 18. To this end, said reinforcement may be fitted with a rail 19 and a carriage 20, mobile on said rail, whereas said device 17 is supported at the carriage 20 by a framework 21, possibly orientable, notably freely, under the effect of the loads inflicted by the animal to the device 17.

Said facility may also comprise a receptacle 22 to accommodate said seminal liquid and means for supporting said device 17, notably said framework 21, as tilted towards said receptacle 22. It may, for example, a goblet, independent from said device. The seminal liquid may then flow by gravity.

Said facility may also comprise a filter, not represented, between said device 17 and said receptacle 22.

Said reinforcement may be made tiltable using a system hinges attached to the ground, thereby facilitating its cleaning and its disinfection.

The invention finally concerns a usage of the device 17 and/or of the facility described above for collecting boar seminal liquid.

Other embodiments and/or other applications, understandable to the man of the art, could also be contemplated, without departing from the framework of the invention.

I claim:

1. A device for sampling seminal liquid of an animal comprising:

a housing having an interior suitable for accommodating a penis of the animal, said housing emulating a shape of a vagina of the animal, said interior being substantially helicoidal in shape, said housing having walls extending around said interior; and an ejaculation-triggering means attachable to said walls of said housing for subjecting said walls to pulses suitable for stimulating the penis of the animal so as to trigger an ejaculation.

2. The device of claim 1, said housing extending longitudinally between an introduction orifice and an evacuation orifice.

3. The device of claim 2, said ejaculation-triggering means for causing a substantially radial deformation of said walls of said housing over an entire length of said walls.

4. The device of claim 1, said housing comprising:

a tubular flexible membrane defining said interior of said housing;

a rigid sheath receiving said flexible membrane therein, said flexible membrane and said sheath defining a sealed chamber therebetween, said chamber having air therein; and pressurizing means cooperative with said chamber for varying a pressure of the air in said chamber.

5. The device of claim 1, said housing having a narrowed section suitable for localized stimulation of the penis.

6. The device of claim 4, said flexible member being coated with a protection film.

7. The device of claim 1, further comprising:

a sampling means cooperative with said housing for sampling the seminal liquid.

8. The device of claim 7 further comprising:

a reinforcement affixed to said sampling means such that said sampling means is mobile with respect to said reinforcement.

9. The device of claim 7, said sampling means comprising:

a receptacle suitable for receiving the seminal fluid; and a supporting means connected to said housing for supporting said housing in tilted fashion toward said receptacle.

10. The device of claim 9, said sampling means further comprising:

a filter positioned between said housing and said receptacle.

* * * * *